United States Patent [19]

Stark et al.

[11] Patent Number: 5,306,695

[45] Date of Patent: Apr. 26, 1994

[54] HALOALKOXY-SUBSTITUTED BENZOYLCYCLOHEXANEDIONES AS HERBICIDES AND PLANT GROWTH REGULATORS

[75] Inventors: Herbert Stark, Kelkheim (Taunus); Klaus Bauer, Hanau; Hermann Bieringer, Eppstein/Taunus, all of Fed. Rep. of Germany

[73] Assignee: Hoechst Aktiengesellschaft, Frankfurt am Main, Fed. Rep. of Germany

[21] Appl. No.: 846,003

[22] Filed: Mar. 4, 1992

[30] Foreign Application Priority Data

Mar. 6, 1991 [DE] Fed. Rep. of Germany ....... 4107141

[51] Int. Cl.$^5$ ..................... A01N 31/04; C07C 205/06
[52] U.S. Cl. .................... 504/348; 504/310; 504/333; 558/415; 568/31; 568/42; 568/306; 568/329
[58] Field of Search .............. 71/123; 568/306, 329, 568/31, 42; 558/415; 504/310, 333, 348

[56] References Cited

U.S. PATENT DOCUMENTS

| | | | |
|---|---|---|---|
| 4,780,127 | 10/1988 | Michaely et al. | 71/103 |
| 4,781,751 | 11/1988 | Chin | 71/103 |
| 4,806,146 | 2/1989 | Carter | 71/98 |
| 4,816,066 | 3/1989 | Michaely et al. | 71/123 |
| 4,838,932 | 6/1989 | Knudsen | 71/98 |
| 4,921,526 | 5/1990 | Lee et al. | 71/86 |
| 4,946,981 | 8/1990 | Carter et al. | 558/415 |
| 4,960,841 | 10/1990 | Kawakata et al. | 525/537 |

FOREIGN PATENT DOCUMENTS

| | | |
|---|---|---|
| 51337/85 | 6/1986 | Australia . |
| 0090262 | 10/1983 | European Pat. Off. . |
| 0135191 | 3/1985 | European Pat. Off. . |
| 0137963 | 4/1985 | European Pat. Off. . |
| 0186118 | 7/1986 | European Pat. Off. . |
| 0186119 | 7/1986 | European Pat. Off. . |
| 0186120 | 7/1986 | European Pat. Off. . |
| 0264737 | 4/1988 | European Pat. Off. . |
| 0268765 | 6/1988 | European Pat. Off. . |
| 0278742 | 8/1988 | European Pat. Off. . |
| 0319075 | 6/1989 | European Pat. Off. . |
| 88/0911 | 2/1988 | South Africa . |

Primary Examiner—Mary C. Lee
Assistant Examiner—Jacqueline Haley
Attorney, Agent, or Firm—Curtis, Morris & Safford

[57] ABSTRACT

Compounds of the formula I

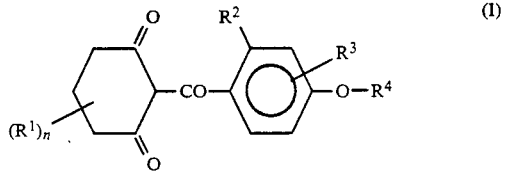

in which n is 0-6, $R^1$ is alkyl, haloalkyl, cycloalkyl, halocycloalkyl, phenyl or halogenated phenyl, $R^2$ is Hal, CN, alkyl, haloalkyl, alkoxy, haloalkoxy, thioalkyl, $R^aSO_2-$, $R^aSO_2O-$, $R^aSO_2NR^6$, $R^a$ and $R^b$ being alkyl or haloalkyl, and $R^3$ is H, Hal, alkyl, haloalkyl, alkoxy, haloalkoxy or alkylthio, and $R^4$ is haloalkyl, are suitable as selective herbicides and as growth regulators. To prepare them, a cyclohexanedione can be reacted a) with a 4-oxy-substituted benzoyl chloride and the resulting enol ether can be rearranged, or b) with a benzoyl cyanide. The benzoyl chloride or benzoyl cyanide required can be obtained from correspondingly substituted toluenes via the carboxylic acid.

11 Claims, No Drawings

HALOALKOXY-SUBSTITUTED BENZOYLCYCLOHEXANEDIONES AS HERBICIDES AND PLANT GROWTH REGULATORS

DESCRIPTION

It has been disclosed that some benzoylated cyclohexanediones have herbicidal and plant-growth-regulating properties; compare, for example, U.S. Pat. No. 4,780,127, EP-A-278,742 (ZA-A-88/911), EP-A-268,795 (U.S. Pat. No. 4,960,841), EP-A-264,859 (U.S. Pat. No. 4,781,751), EP-A-264,737 (U.S. Pat. No. 4,838,932), EP-A-135,191 (U.S. Pat. No. 4,816,066), EP-A-137,963 (U.S. Pat. No. 4,780,127), EP-A-186,118 (U.S. Pat. No. 4,946,981), EP-A-186,119 (AU-A-85/51337), EP-A-90,262 (CA-A-1,217,204) and EP-A-186,120 (U.S. Pat. No. 4,806,146). However, the action of these compounds is not always satisfactory.

Surprisingly, it has now been found that some benzoylated cyclohexanediones which have halogenated alkoxy radicals in the 4-position on the phenyl ring are particularly suitable as herbicides and plant growth regulators.

The present invention therefore relates to compounds of the formula (I) or salts thereof, (I)

in which n is an integer from 0 to 6, $R^1$ represents identical or different substituents selected from the group consisting of straight-chain $C_1$-$C_4$-alkyl, branched $C_3$-$C_4$-alkyl, $C_3$-$C_6$-cycloalkyl and phenyl, the abovementioned radicals being unsubstituted or substituted by one or more halogen atoms, $R^2$ is halogen, $NO_2$, CN, $C_1$-$C_3$-alkyl, $C_1$-$C_3$-haloalkyl, $C_1$-$C_3$-alkoxy, $C_1$-$C_3$-haloalkoxy, $C_1$-$C_3$-thioalkyl, $R^aSO_2$—, $R^aSO_2$—O—, $R^aSO_2NR^b$—, where $R^a$ and $R^b$ independently of one another are $C_1$-$C_2$-alkyl or $C_1$-$C_2$-haloalkyl, $R^3$ is hydrogen, halogen, $C_1$-$C_3$-alkyl, $C_1$-$C_3$-haloalkyl, $C_1$-$C_3$-alkoxy, $C_1$-$C_3$-haloalkoxy or $C_1$-$C_3$-alkylthio and $R^4$ $C_1$-$C_3$-haloalkyl.

Unless otherwise stated, alkyl, alkoxy, haloalkyl, alkylamino and alkylthio radicals as well as the corresponding unsaturated and/or substituted radicals in formula (I) can in each case be straight-chain or branched. Alkyl radicals, also in composite meanings such as, inter alia, alkoxy and haloalkyl, are, for example, methyl, ethyl, n- or i-propyl, n-, i-, t- or 2-butyl; Halogen is fluorine, chlorine, bromine or iodine.

Depending on position and number of the radicals $R^1$, compounds of the formula (I) can be stereoisomeric. The invention therefore relates to all stereoisomers which are embraced by the general formula (I), and mixtures of these.

Due to tautomerism equilibriums, the compounds of the formula (I) according to the invention can have the following 3 structures:

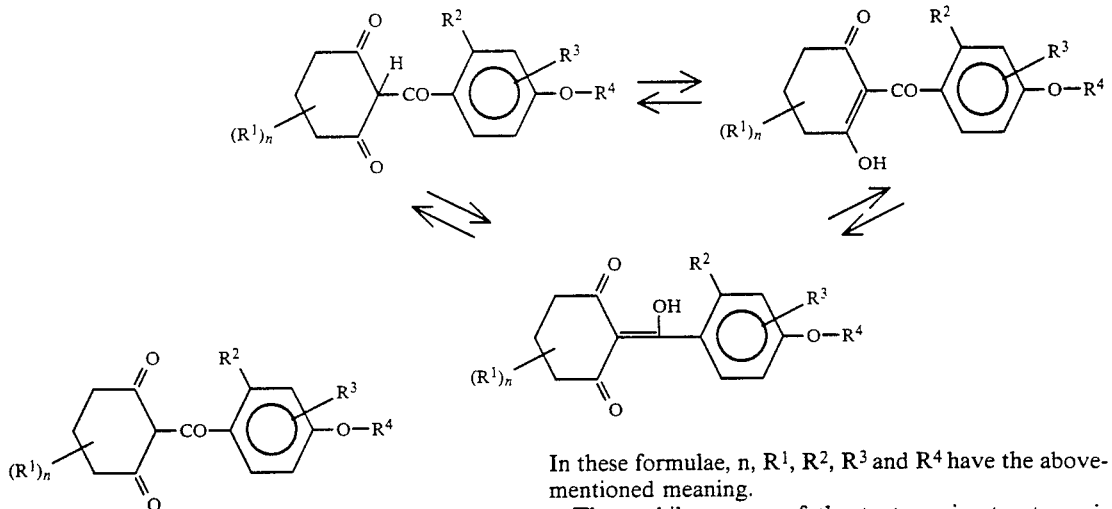

In these formulae, n, $R^1$, $R^2$, $R^3$ and $R^4$ have the abovementioned meaning.

The mobile proton of the tautomeric structures is acidic and can be removed by reaction with a base. The anion of the salt formed in this process can have the following resonance structures:

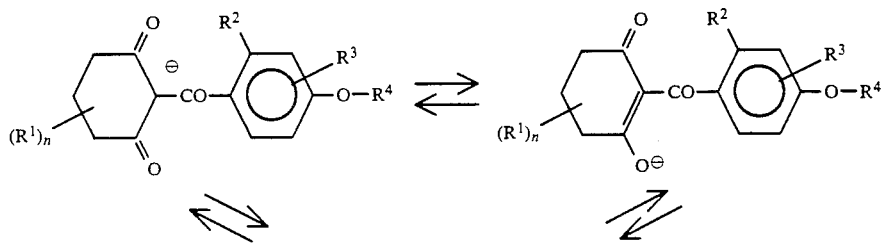

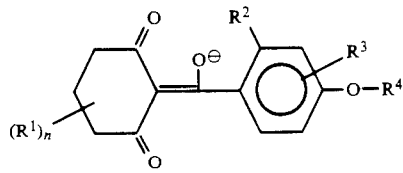

In these formulae, n, $R^1$, $R^2$, $R^3$ and $R^4$ have the abovementioned meaning.

Examples of suitable counterions to these anions are inorganic cations such as the cations of the alkali metals, for example lithium, sodium and potassium, or alkaline earth metals, for example calcium and magnesium, or ammonium or organic cations, such as substituted ammonium, sulfonium, sulfoxonium or phosphonium. The invention therefore also preferably embraces these salts of the compounds of the formula (I).

Compounds of the formula (I) or salts thereof which are of particular interest are those in which n is an integer from 0 to 4, preferably 0 to 3, $R^1$ represents identical or different substituents selected from the group consisting of straight-chain $C_1$-$C_3$-alkyl, i-propyl, $C_4$-$C_6$-cycloalkyl and phenyl, the above 4 radicals being unsubstituted or substituted by one or more radicals selected from the group consisting of chlorine and fluorine, $R^2$ is halogen, $NO_2$, CN, $C_1$-$C_3$-alkyl, $C_1$-$C_3$-haloalkyl, $C_1$-$C_2$-alkoxy, $C_1$-$C_2$-haloalkoxy, $R^aSO_2$—, where $R^4$ has the abovementioned meaning, $R^3$ is H, halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio and $R^4$ is $C_1$-$C_3$-haloalkyl, preferably $C_1$-$C_2$-haloalkyl.

n is preferably 0 to 3;

$R^1$ is preferably $C_1$-$C_3$-alkyl, in particular methyl, ethyl or i-propyl, cyclopentyl or phenyl;

$R^2$ is preferably fluorine, chlorine, $NO_2$, CN, methyl, trifluoromethyl, methoxy, difluoromethoxy, trifluoromethoxy or methylsulfonyl;

$R^3$ is preferably hydrogen, halogen, for example fluorine or chlorine, methyl, $CF_3$, methoxy, difluoromethoxy, trifluoromethoxy or methylthio, in particular hydrogen;

$R^4$ is, for example, $CH_2F$, $CHF_2$, $CH_2Cl$, $CHCl_2$, $CCl_3$, $CH_2CH_2Cl$, $CH_2CH_2F$, $CH_2CHF_2$, $CH_2CF_3$, CHF—$CH_3$, CHF—$CH_2F$, $CHFCHF_2$, $CF_2$—$CH_3$, $CF_2CH_2F$, $CF_2CHF_2$, $CF_2$—$CF_3$, $CF_2CHFCl$, $CHFCHFCl$, $CH_2CCl_3$, $CH_2CHCl_2$, $CHFCHCl_2$, $CF_2CHCl_2$, $CHFCH_2Cl$ or $CF_2CH_2Cl$, $R^4$ is, in particular, $CH_2F$ $CHF_2$, $CH_2CF_3$, $CF_2CHF_2$, $CF_2CHFCl$ or $CH_2CH_2Cl$ very particularly $CHF_2$.

Other preferred compounds of the formula (I) according to the invention or salts thereof are those in which the abovementioned preferred characteristics are combined.

The present invention furthermore relates to processes for the preparation of the compounds of the abovementioned formula (I) or the salts thereof, which comprises a) reacting a cyclohexanedione of the formula (II)

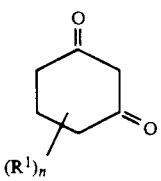

with an acid chloride of the formula (III)

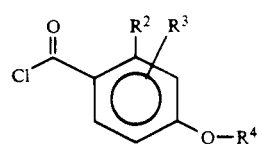

to give an enol ether of the formula (IV)

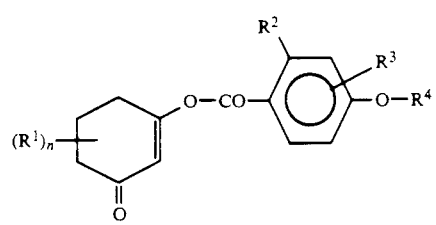

and rearranging the latter in the presence of a cyanide source (for example acetone cyanohydrin) or a Lewis acid (for example $AlCl_3$) to give a compound of the abovementioned formula (I)

or b) reacting a cyclohexanedione of the abovementioned formula (II) with a benzoyl cyanide of the formula (V)

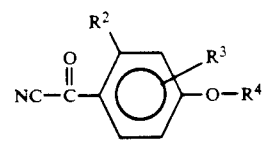

where, in formulae (II) to (V), $R^1$, $R^2$, $R^3$, $R^4$ and n have the meaning mentioned in formula (I).

The acid chlorides of the formula (III) can be prepared from the carboxylic acids of the formula (VI)

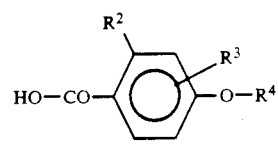

by, or analogously to, processes known from the literature (cf., for example, Fieser u. Fieser, Reagents for Organic Synthesis, Vol. I, p. 1158-1159 (1967), ibid. p. 767-769).

The reaction of the compounds of the formulae (II) and (III) by variant a) is generally carried out in the presence of an organic solvent, for example a protic or aprotic solvent. Examples of suitable solvents are aromatic or aliphatic, optionally halogenated, hydrocarbons, ethers, esters, nitriles, formamides, lactones and alcohols, and mixtures of the abovementioned solvents. Preferred solvents are aprotic, dipolar solvents such as ether, acetonitrile and dimethylformamide, and mixtures of the solvents. The reaction is preferably carried out in the presence of an organic or inorganic base, preferably a sterically hindered organic base selected from the group comprising the substituted amines, such as triethylamine or 1,8-diazabicyclo[5,4,0]-undec-7-ene.

The reaction temperature is generally −20° C. to the boiling point of the solvent, preferably 15° C. to 40° C. The rearrangement reaction of the intermediate of the formula (IV) from the reaction of (II) and (III) is preferably carried Out without prior isolation of the intermediate by adding a cyanide source or a Lewis acid to the reaction mixture obtained f rom the reaction of (II) and (III) at −20° C. to the boiling point of the solvent, preferably at 15° to 30° C. A suitable cyanide source is, for example, acetone cyanohydrin, and a suitable Lewis acid is, for example, $AlCl_3$.

After the rearrangement reaction, the product can be isolated by customary methods, for example by extracting the reaction mixture which has been rendered aqueousacidic with an organic solvent and crystallization.

The reaction of the compounds of the formulae (II) and (V) by variant b) are generally also carried out in an is organic solvent, suitable solvents being those mentioned for the process by variant a). Preferred reaction temperatures are those from 0° C. to the boiling point of the solvent, in particular 15° C. to 80° C.

The benzoyl cyanides (V) can be prepared from the carboxylic acids (VI) by processes known from the literature (cf., for example, Oakwood, Weisgerber, Organic Synthesis, col. Vol. III, P, 112 (1955)).

A large number of methods for the preparation of substituted benzoic acids has been described in the chemical specialist literature. These are also suitable for the preparation of the acids of the formula (VI). A frequently used method is the oxidation Of toluenes of the formula (VII) (for example using potassium permanganate or nitric acid):

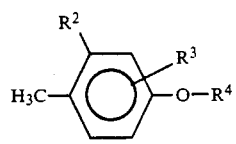

(VII)

The carboxylic acids of the formula (VI), their salts with inorganic and organic bases and their reactive derivatives of the formula (III) and (V) are novel compounds. The present invention therefore also relates to the compounds of the formula (VIII)

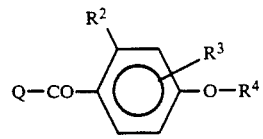

(VIII)

in which Q is Cl, CN, OH or $O^-Me^+$, $Me^+$ being an inorganic or organic cation, and $R^2$, $R^3$, and $R^4$ have the abovementioned meaning.

The compounds of the formula (I) according to the invention have an excellent herbicidal activity against a broad range of economically important monocotyledon and dicotyledon harmful plants. The active substances also act efficiently on perennial weeds which produce shoots from rhizomes, rootstocks or other perennial organs and which are difficult to control. In this context, it does not matter whether the substances are applied before sowing, preemergence or post-emergence. Specifically, examples may be mentioned of some representatives of the monocotyledon and dicotyledon weed flora which can be controlled by the compounds according to the invention, without these being a restriction to certain species.

Examples of weed species on which the active substance acts efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledon weed species, the range of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The active substances according to the invention likewise effect outstanding control of weeds which occur under the specific conditions of rice growing, such as, for example, Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active substances are applied post-emergence on the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

Although the compounds according to the invention have an excellent herbicidal activity against monocotyledon and dicotyledon weeds, crop plants of economically important crops, such as, for example, wheat, barley, rye, rice, maize, sugar beet, cotton and soya, are damaged not at all, or only to a negligible extent. For these reasons, the present compounds are highly suitable for selectively controlling undesired plant growth in plantings for agricultural use.

In addition, the substances according to the invention have excellent growth-regulating properties in crop plants. They engage in the plant metabolism in a regulating manner and can thus be employed for the targeted control of plant constituents and for facilitating harvesting, such as, for example, by provoking desiccation and stunted growth. Furthermore, they are also suitable for generally regulating and inhibiting undesired vegetative growth, without simultaneously destroying the plants. Inhibition of vegetative growth plays an important role in many monocotyledon and dicotyledon crops because lodging can be reduced hereby, or prevented completely.

The compounds according to the invention can be employed in the conventional preparations as wettable powders, emulsifiable concentrates, sprayable solutions, dusts or granules. The invention therefore also relates to herbicidal and plant-growth-regulating compositions which comprise compounds of the formula (I) or salts thereof.

The compounds of the formula (I) can be formulated in various ways, depending on the prevailing biological and/or chemics-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing agents, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and described, for example, in: Winnacker-Küchler, "Chemische Technologie" [Chemical Technology], Volume 7, C. Hauser Verlag, Munich, 4th Edition 1986; van Valkenburg, "Pesticides Formulations" Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H.v. Olphen, "Introduction to Clay Colloid Chemistry"; 2nd Ed., j. Wiley & Sons, N.Y.; Marsden, "Solvents Guide", 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene oxide adducts], Wiss. VerlagBgesell., Stuttgart 1976; Winnacker-Küchler, "Chemische Technologic" [Chemical Technology], Volume 7, C. Hauser Verlag, Munich, 4th Ed. 1986.

Based on these formulations, it is also possible to prepare combinations with other pesticidally active substances, fertilizers and/or growth regulators, for example in the form of a readymix or a tank mix.

Wettable powders are preparations which are uniformly dispersible in water and which, besides the active substance, also contain wetting agents, for example, polyoxyethylated alkylphenols, polyoxyethylated fatty alcohols and fatty amines, fatty alcohol polyglycol ether sulfates, alkanesulfonates or alkylbenzenesulfonates, and dispersing agents, for example sodium ligninsulfonate, sodium 2,2'-dinaphthylmethane-6,6'-disulfonate, sodium dibutylnaphthalenesulfonate and also sodium oleoylmethyltaurinate, in addition to a diluent or inert substance.

Emulsifiable concentrates can be prepared, for example, by dissolving the active substance in an organic solvent, for example butanol, cyclohexanone, dimethylformamide, xylene and also higher-boiling aromatics or hydrocarbons, with the addition of one or more emulsifiers. Emulsifiers which can be used are, for example: calcium salts of alkylarylsulfonic acids, such as calcium dodecylbenzenesulfonate or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusts are obtained by grinding the active substance with finely divided solid substances, for example talc or natural clays, such as kaolin, bentonite or pyrophillite, or diatomaceous earth.

Granules can be produced either by spraying the active substance onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

The agrochemical preparations generally comprise 0.1 to 99 percent by weight, in particular 0.1 to 95% by weight, of active substance of the formula (I).

The active substance concentration in wettable powders is, for example, about 10 to 90% by weight; the remainder to 100% by weight is composed of conventional formulation components. In the case of emulsifiable concentrates, the active substance concentration can be about 1 to 85% by weight. Formulations in the form of dusts usually contain 1 to 25% by weight of active substance, sprayable solutions about 0.2 to 20% by weight. In the case of granules, the active substance content depends partly on whether the active compound is liquid or solid. It is generally between 10 and 90% by weight in the case of the water-dispersible granules.

In addition, the active substance formulations mentioned comprise, if appropriate, the adhesives, wetting agents, dispersing agents, emulsifiers, penetrants, solvents, fillers or carriers which are conventional in each case.

For use, the formulations present in commercially available form are diluted, if appropriate, in a conventional manner, for example using water in the case of wettable powders, emulsifiable concentrates, dispersions and water-dispersible granules. Preparations in the form of dusts and granules for broadcasting or soil application and also sprayable solutions are usually not further diluted with other inert substances before use.

The application rate of the compounds of the formula (I) required varies with the external conditions, such as temperature, humidity and the nature of the herbicide used, amongst others. It can vary within wide limits, for example between 0.001 and 10.0 kg/ha or more of active ingredient, preferably, however, it is between 0.005 and 5 kg/ha.

If appropriate, mixtures or mixed formulations with other active substances, such as, for example, insecticides, acaricides, herbicides, safeners, fertilizers, growth regulators or fungicides are also possible.

A. Chemical Examples

Example A:
2-(2-Chloro-4-difluoromethoxy-benzoyl)-cyclohexane-1,3-dione (compound No. 18):

7.23 g of 2-chloro-4-difluoromethoxybenzoyl chloride and 2.80 g of 1,3-cyclohexanedione are introduced into 30 ml of acetonitrile, and 6.32 g of triethylamine is added dropwise in such a manner that the internal temperature does not exceed 40° C. The mixture is subsequently stirred for 15 minutes at room temperature, 1.95 g of acetone cyanohydrin are added, and stirring is continued for 3 hours at room temperature. The reaction mixture is diluted with 100 ml of ethyl acetate and 50 ml of 1N hydrochloric acid are added. After vigorous shaking, the phases are separated, and the organic phase is extracted twice with 50 ml portions of 5% strength potassium carbonate solution. The combined aqueous phases are acidified using concentrated hydrochloric acid and reextracted using dichloromethane (2 times 50 ml). The mixture is dried over magnesium sulfate, the solvent is stripped off, and 6.9 g (87% of theory) of 2-(2-chloro-4-difluoromethoxybenzoyl)-cyclohexane-1,3-dione are then obtained as pale yellow crystals of melting point 68°–72° C.

Example B:
2-(2-nitro-4-difluoromethoxybenzoyl)-4,4,6-trimethyl-cyclohexane-1,3-dione (compound No. 71)

5.03 g of 2-nitro-4-difluoromethoxybenzoyl chloride and 2.57 g of 4,4,6-trimethylcyclohexane-1,3-dione are introduced into 20 ml of acetonitrile, and 4.21 g of triethylamine are added dropwise in such a way that the internal temperature does not exceed 40° C. The mixture is subsequently stirred for 15 minutes at room temperature, 1.29 g of acetone cyanohydrin are added, and stirring is continued for 3 hours at room temperature. The reaction mixture is diluted with 100 ml of ethyl acetates and 50 ml of 1N hydrochloric acid are added. After vigorous shaking, the phases are separated, the organic phases are dried over MgSO$_4$, and the solvent is stripped off under reduced pressure. The oil which remains (7.1 g) is chromatographed on silica gel using ethyl acetate/petroleum ether 1:2 as the eluent. This gives 3.28 g (46% of theory) of 2-(2-nitro-4-difluoromethoxy-benzoyl)-4,4,6-trimethylcyclohexane-1,3-dione of melting point 108°–110° C.

Example C: 2-nitro-4-difluoromethoxybenzoyl chloride 23.3 g of 2-nitro-4-fluoromethoxybenzoic acid and 16 g of thionyl chloride are refluxed for 7 hours with 200 mg of dimethylformamide. The reaction mixture is subsequently distilled under reduced pressure. This gives 23.7 g of product of boiling point 101°–105° C. at 0.4 mbar.

Example D: 2-nitro-4-difluoromethoxybenzoic acid 72.1 g of 2-nitro-4-difluoromethoxytoluene and 300 ml of pyridine are refluxed. A solution of 336 g of potassium permanganate in 500 ml of water is then added in portions. The batch is subsequently held for a further 7 hours at 80° C. When cold, 500 ml of 2N sodium hydroxide solution are added, the mixture is extracted with ether, and the aqueous phase is acidified with concentrated hydrochloric acid. During this process, the product separates out as an oil which crystallizes on prolonged stirring. After filtration, washing with dilute hydrochloric acid and drying, 53.6 g of desired product are obtained in the form of white crystals (m.p. 136°–138° C.).

The compounds from Table 1 below are obtained analogously to the processes described in Examples A and B. The benzoyl chlorides used in these processes are obtained analogously to the processes of Examples C and D.

TABLE 1

Compounds of the formula (I) according to the invention

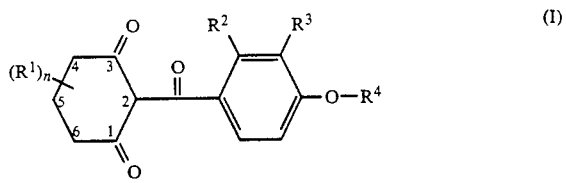

(I)

| No. | R$^1$ | n | R$^2$ | R$^3$ | O—R$^4$ | m.p. |
|---|---|---|---|---|---|---|
| 1 | | 0 | F | H | OCH$_2$F | |
| 2 | | 0 | F | H | OCHF$_2$ | 122–123 |
| 3 | 4-CH$_3$ | 1 | F | H | OCHF$_2$ | |
| 4 | 5-CH$_3$ | 1 | F | H | OCHF$_2$ | |
| 5 | 4,4-(CH$_3$)$_2$ | 2 | F | H | OCHF$_2$ | 123–124 |
| 6 | 5,5-(CH$_3$)$_2$ | 2 | F | H | OCHF$_2$ | |
| 7 | 4,5-(CH$_3$)$_2$ | 2 | F | H | OCHF$_2$ | |
| 8 | 4,6-(CH$_3$)$_2$ | 2 | F | H | OCHF$_2$ | |
| 9 | 4,4,5-(CH$_3$)$_3$ | 3 | F | H | OCHF$_2$ | |
| 10 | 4,4,6-(CH$_3$)$_3$ | 3 | F | H | OCHF$_2$ | |
| 11 | 4,5,5-(CH$_3$)$_3$ | 3 | F | H | OCHF$_2$ | |
| 12 | 4,5,6-(CH$_3$)$_3$ | 3 | F | H | OCHF$_2$ | |
| 13 | | 0 | F | Cl | OCHF$_2$ | |
| 14 | | 0 | F | CH$_3$ | OCHF$_2$ | |
| 15 | | 0 | F | CF$_3$ | OCHF$_2$ | |
| 16 | | 0 | F | OCH$_3$ | OCHF$_2$ | |
| 17 | | 0 | Cl | H | OCH$_2$F | |
| 18 | | 0 | Cl | H | OCHF$_2$ | 68–72 |

TABLE 1-continued

Compounds of the formula (I) according to the invention $$(R^1)_n \begin{array}{c} \text{cyclohexane-1,3-dione} \end{array} - C(=O) - \text{aryl}(R^2, R^3) - O - R^4 \quad (I)$$

| No. | R¹ | n | R² | R³ | O—R⁴ | m.p. |
|---|---|---|---|---|---|---|
| 19 |  | 0 | Cl | H | OCH₂CF₃ |  |
| 20 |  | 0 | Cl | H | OCF₂CHF₂ |  |
| 21 |  | 0 | Cl | H | OCF₂CHFCl |  |
| 22 |  | 0 | Cl | H | OCH₂CH₂Cl |  |
| 23 | 4-CH₃ | 1 | Cl | H | OCHF₂ | oil |
| 24 | 4-CH₃ | 1 | Cl | H | OCH₂F |  |
| 25 | 5-CH₃ | 1 | Cl | H | OCHF₂ |  |
| 26 | 5-CH₃ | 1 | Cl | H | OCH₂F |  |
| 27 | 4,4-(CH₃)₂ | 2 | Cl | H | OCHF₂ | oil |
| 28 | 4,4-(CH₃)₂ | 2 | Cl | H | OCH₂F |  |
| 29 | 5,5-(CH₃)₂ | 2 | Cl | H | OCHF₂ | oil |
| 30 | 5,5-(CH₃)₂ | 2 | Cl | H | OCH₂F |  |
| 31 | 4,5-(CH₃)₂ | 2 | Cl | H | OCHF₂ | oil |
| 32 | 4,6-(CH₃)₂ | 2 | Cl | H | OCHF₂ | 114 |
| 33 | 4,4,5-(CH₃)₃ | 3 | Cl | H | OCHF₂ | oil |
| 34 | 4,4,5-(CH₃)₃ | 3 | Cl | H | OCH₂F |  |
| 35 | 4,4,6-(CH₃)₃ | 3 | Cl | H | OCHF₂ | 108–110 |
| 36 | 4,4,6-(CH₃)₃ | 3 | Cl | H | OCH₂F |  |
| 37 | 4,5,5-(CH₃)₃ | 3 | Cl | H | OCHF₂ |  |
| 38 | 4,5,6-(CH₃)₃ | 3 | Cl | H | OCHF₂ |  |
| 39 | 4-CH₂CH₃ | 1 | Cl | H | OCHF₂ | 125 |
| 40 | 4-CH(CH₃)₂ | 1 | Cl | H | OCHF₂ | oil |
| 41 | 4-Cyclopentyl | 1 | Cl | H | OCHF₂ |  |
| 42 | 4-Ph | 1 | Cl | H | OCHF₂ | oil |
| 43 | 5-CH(CH₃)₂ | 1 | Cl | H | OCHF₂ |  |
| 44 |  | 0 | Cl | F | OCHF₂ |  |
| 45 |  | 0 | Cl | Cl | OCH₂F |  |
| 46 |  | 0 | Cl | Cl | OCHF₂ |  |
| 47 |  | 0 | Cl | CH₃ | OCHF₂ |  |
| 48 | 4,4-(CH₃)₂ | 2 | Cl | CH₃ | OCHF₂ |  |
| 49 |  | 0 | Cl | CF₃ | OCHF₂ |  |
| 50 |  | 0 | Cl | OCH₃ | OCHF₂ |  |
| 51 |  | 0 | Cl | OCHF₂ | OCHF₂ |  |
| 52 |  | 0 | Cl | SCH₃ | OCHF₂ |  |
| 53 |  | 0 | NO₂ | H | OCH₂F |  |
| 54 |  | 0 | NO₂ | H | OCHF₂ | oil |
| 55 |  | 0 | NO₂ | H | OCH₂CF₃ |  |
| 56 |  | 0 | NO₂ | H | OCF₂CHF₂ |  |
| 57 |  | 0 | NO₂ | H | OCF₂CHFCl | 130 (decomp.) |
| 58 |  | 0 | NO₂ | H | OCH₂CH₂Cl |  |
| 59 | 4-CH₃ | 1 | NO₂ | H | OCHF₂ | oil |
| 60 | 4-CH₃ | 1 | NO₂ | H | OCH₂F |  |
| 61 | 5-CH₃ | 1 | NO₂ | H | OCHF₂ | 120–122 |
| 62 | 5-CH₃ | 1 | NO₂ | H | OCH₂F |  |
| 63 | 4,4-(CH₃)₂ | 2 | NO₂ | H | OCHF₂ | oil |
| 64 | 4,4-(CH₃)₂ | 2 | NO₂ | H | OCH₂F |  |
| 65 | 5,5-(CH₃)₂ | 2 | NO₂ | H | OCHF₂ |  |
| 66 | 5,5-(CH₃)₂ | 2 | NO₂ | H | OCH₂F |  |
| 67 | 4,5-(CH₃)₂ | 2 | NO₂ | H | OCHF₂ | oil |
| 68 | 4,6-(CH₃)₂ | 2 | NO₂ | H | OCHF₂ |  |
| 69 | 4,4,5-(CH₃)₃ | 3 | NO₂ | H | OCHF₂ | oil |
| 70 | 4,4,5-(CH₃)₃ | 3 | NO₂ | H | OCH₂F |  |
| 71 | 4,4,6-(CH₃)₃ | 3 | NO₂ | H | OCHF₂ | oil |
| 72 | 4,4,6-(CH₃)₃ | 3 | NO₂ | H | OCH₂F |  |
| 73 | 4,5,5-(CH₃)₃ | 3 | NO₂ | H | OCHF₂ |  |
| 74 | 4,5,6-(CH₃)₃ | 3 | NO₂ | H | OCHF₂ |  |
| 75 | 4-CH₂CH₃ | 1 | NO₂ | H | OCHF₂ |  |
| 76 | 4-CH(CH₃)₂ | 1 | NO₂ | H | OCHF₂ | oil |
| 77 | 4-Cyclopentyl | 1 | NO₂ | H | OCHF₂ |  |
| 78 | 4-Ph | 1 | NO₂ | H | OCHF₂ | 170 |
| 79 | 5-CH(CH₃)₂ | 1 | NO₂ | H | OCHF₂ |  |
| 80 |  | 0 | NO₂ | F | OCHF₂ |  |
| 81 |  | 0 | NO₂ | Cl | OCH₂F |  |
| 82 |  | 0 | NO₂ | Cl | OCHF₂ |  |
| 83 |  | 0 | NO₂ | CH₃ | OCHF₂ |  |
| 84 | 4,4-(CH₃)₂ | 2 | NO₂ | CH₃ | OCHF₂ |  |
| 85 |  | 0 | NO₂ | CF₃ | OCHF₂ |  |
| 86 |  | 0 | NO₂ | OCH₃ | OCHF₂ |  |
| 87 |  | 0 | NO₂ | OCHF₂ | OCHF₂ |  |

TABLE 1-continued
Compounds of the formula (I) according to the invention $$(R^1)_n \underset{6}{\overset{4}{\underset{5}{\bigcirc}}} \underset{1}{\overset{3}{\underset{2}{\bigcirc}}} \overset{O}{\underset{O}{\|}} \overset{O}{\underset{\|}{C}} \overset{R^2 \ R^3}{\underset{}{\bigcirc}} O-R^4 \quad (I)$$

| No. | $R^1$ | n | $R^2$ | $R^3$ | $O-R^4$ | m.p. |
|---|---|---|---|---|---|---|
| 88 | | 0 | $NO_2$ | $SCH_3$ | $OCHF_2$ | |
| 89 | | 0 | CN | H | $OCH_2F$ | |
| 90 | | 0 | CN | H | $OCHF_2$ | |
| 91 | 4-$CH_3$ | 1 | CN | H | $OCHF_2$ | |
| 92 | 5-$CH_3$ | 1 | CN | H | $OCHF_2$ | |
| 93 | 4,4-$(CH_3)_2$ | 2 | CN | H | $OCHF_2$ | |
| 94 | 5,5-$(CH_3)_2$ | 2 | CN | H | $OCHF_2$ | |
| 95 | 4,4,5-$(CH_3)_3$ | 3 | CN | H | $OCHF_2$ | |
| 96 | 4,4,6-$(CH_3)_3$ | 3 | CN | H | $OCHF_2$ | |
| 97 | | 0 | CN | Cl | $OCHF_2$ | |
| 98 | | 0 | CN | $CH_3$ | $OCHF_2$ | |
| 99 | | 0 | CN | $OCH_3$ | $OCHF_2$ | |
| 100 | | 0 | $CH_3$ | H | $OCH_2F$ | |
| 101 | | 0 | $CH_3$ | H | $OCHF_2$ | |
| 102 | 4-$CH_3$ | 1 | $CH_3$ | H | $OCHF_2$ | |
| 103 | 5-$CH_3$ | 1 | $CH_3$ | H | $OCHF_2$ | |
| 104 | 4,4-$(CH_3)_2$ | 2 | $CH_3$ | H | $OCHF_2$ | |
| 105 | 5,5-$(CH_3)_2$ | 2 | $CH_3$ | H | $OCHF_2$ | |
| 106 | 4,4,5-$(CH_3)_3$ | 3 | $CH_3$ | H | $OCHF_2$ | |
| 107 | 4,4,6-$(CH_3)_3$ | 3 | $CH_3$ | H | $OCHF_2$ | |
| 108 | | 0 | $CH_3$ | Cl | $OCHF_2$ | |
| 109 | | 0 | $CH_3$ | $OCH_3$ | $OCHF_2$ | |
| 110 | | 0 | $CF_3$ | H | $OCH_2F$ | |
| 111 | | 0 | $CF_3$ | H | $OCHF_2$ | |
| 112 | 4-$CH_3$ | 1 | $CF_3$ | H | $OCHF_2$ | |
| 113 | 5-$CH_3$ | 1 | $CF_3$ | H | $OCHF_2$ | |
| 114 | 4,4-$(CH_3)_2$ | 2 | $CF_3$ | H | $OCHF_2$ | |
| 115 | 5,5-$(CH_3)_2$ | 2 | $CF_3$ | H | $OCHF_2$ | |
| 116 | 4,4,5-$(CH_3)_3$ | 3 | $CF_3$ | H | $OCHF_2$ | |
| 117 | 4,4,6-$(CH_3)_3$ | 3 | $CF_3$ | H | $OCHF_2$ | |
| 118 | | 0 | $CF_3$ | Cl | $OCHF_2$ | |
| 119 | | 0 | $CF_3$ | $OCH_3$ | $OCHF_2$ | |
| 120 | | 0 | $OCH_3$ | H | $OCH_2F$ | |
| 121 | | 0 | $OCH_3$ | H | $OCHF_2$ | |
| 122 | 4-$CH_3$ | 1 | $OCH_3$ | H | $OCHF_2$ | |
| 123 | 4,4-$(CH_3)_2$ | 2 | $OCH_3$ | H | $OCHF_2$ | |
| 124 | 5,5-$(CH_3)_2$ | 2 | $OCH_3$ | H | $OCHF_2$ | |
| 125 | 4,4,5-$(CH_3)_3$ | 3 | $OCH_3$ | H | $OCHF_2$ | |
| 126 | 4,4,6-$(CH_3)_3$ | 3 | $OCH_3$ | H | $OCHF_2$ | |
| 127 | | 0 | $OCHF_2$ | H | $OCHF_2$ | |
| 128 | 4-$CH_3$ | 1 | $OCHF_2$ | H | $OCHF_2$ | |
| 129 | 4,4-$(CH_3)_2$ | 2 | $OCHF_2$ | H | $OCHF_2$ | |
| 130 | 5,5-$(CH_3)_2$ | 2 | $OCHF_2$ | H | $OCHF_2$ | |
| 131 | 4,4,5-$(CH_3)_3$ | 3 | $OCHF_2$ | H | $OCHF_2$ | |
| 132 | 4,4,6-$(CH_3)_3$ | 3 | $OCHF_2$ | H | $OCHF_2$ | |
| 133 | | 0 | $SCH_3$ | H | $OCHF_2$ | |
| 134 | 4,4-$(CH_3)_2$ | 2 | $SCH_3$ | H | $OCHF_2$ | |
| 135 | 4,4,6-$(CH_3)_3$ | 3 | $SCH_3$ | H | $OCHF_2$ | |
| 136 | | 0 | $SO_2CH_3$ | H | $OCH_2F$ | |
| 137 | | 0 | $SO_2CH_3$ | H | $OCHF_2$ | |
| 138 | 4-$CH_3$ | 1 | $SO_2CH_3$ | H | $OCHF_2$ | |
| 139 | 5-$CH_3$ | 1 | $SO_2CH_3$ | H | $OCHF_2$ | |
| 140 | 4,4-$(CH_3)_2$ | 2 | $SO_2CH_3$ | H | $OCHF_2$ | |
| 141 | 5,5-$(CH_3)_2$ | 2 | $SO_2CH_3$ | H | $OCHF_2$ | |
| 142 | 4,4,5-$(CH_3)_3$ | 3 | $SO_2CH_3$ | H | $OCHF_2$ | |
| 143 | 4,4,6-$(CH_3)_3$ | 3 | $SO_2CH_3$ | H | $OCHF_2$ | |
| 144 | | 0 | $SO_2CH_3$ | Cl | $OCHF_2$ | |
| 145 | | 0 | $SO_2CH_3$ | $OCH_3$ | $OCHF_2$ | |

B. Formulation Examples a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing requartz as inert substance, 10 parts by weight of potassium ligninsulfonate and 1 part by weight of sodium oleoylmethyltauride as wetting and dispersing agent, and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight (8 EO) and 71 parts by weight of paraffinic mineral oil (boiling range, for example, approx. 255° to above 277° C.) and grinding the mixture in a ball mill to a fineness of below 5 microns.

d) An emulsifiable concentrate is obtained from 15 parts by weight of a compound of the formula (I), 75 parts by weight of cyclohexane as the solvent and 10 parts by weight of oxyethylated nonylphenol as emulsifier.

e) Water-dispersible granules are obtained by mixing

| 75 | parts by weight | of a compound of the formula (I), |
|----|-----------------|-----------------------------------|
| 10 | " | of calcium ligninsulfonate, |
| 5 | " | of sodium lauryl sulfate, |
| 3 | " | of polyvinyl alcohol and |
| 7 | " | of kaolin | and grinding the mixture in a pinned disc mill, and granulating the powder in a fluidized bed by spraying on water as granulation liquid.

f) Water-dispersible granules are also obtained by homogenizing and precomminuting in a colloid mill

| 25 | parts by weight | of a compound of the formula (I), |
|----|-----------------|-----------------------------------|
| 5 | " | of sodium 2,2'-dinaphthylmethane-6,6'-disulfonate, |
| 2 | " | of sodium oleoylmethyltauride, |
| 1 | part by weight | of polyvinyl alcohol, |
| 17 | parts by weight | of calcium carbonate and |
| 50 | " | of water, | subsequently grinding the mixture in a bead mill and atomizing and drying the resulting suspension in a spray tower by means of a Bingle-substance nozzle.

g) Extruder granules are obtained by mixing 20 parts by weight of active substance, 3 parts by weight of sodium ligninsulfonate, 1 part by weight of carboxymethylcellulose and 76 parts by weight of kaolin, grinding the mixture and moistening it with water. This mixture is extruded and subsequently dried in a stream of air.

C. Biological Examples

The damage to the harmful plants, or the tolerance by the crop plants, was scored using a key in which the effectiveness is expressed by figures from 0 to 5. The figures denote:

0 = no effect
1 = 0 to 20% effect or damage
2 = 20 to 40% effect or damage
3 = 40 to 60% effect or damage
4 = 60 to 80% effect or damage
5 = 80 to 100% effect or damage 1. Preemergence effect on weeds Seeds or rhizome pieces of monocotyledon and dicotyledon weed plants were placed in sandy loam soil in plastic pots and covered with soil. The compounds according to the invention which were formulated in the form of wettable powders or emulsion concentrates were then applied to the surface of the soil cover in the form of aqueous suspensions or emulsions at an application rate of 600 to 800 l of water/ha (converted), in various dosages.

After the treatment, the pots were placed in a greenhouse and kept under good growth conditions for the weeds. After the test plants had emerged, the damage to the plants or the negative effect on the emergence was scored visually after a test period of 3 to 4 weeks by comparison with untreated controls. As shown by the score figures, the compounds according to the invention have a good herbicidal preemergence action against a broad range of grass weeds and dicotyledon weeds (cf. Table 2).

TABLE 2

Pre-emergence effect of compounds according to the invention

| Ex. No. | Dosage rate (kg of a.i./ha) | STME | CRSE | SIAL | LOMU | ECCR | AVSA |
|---------|------|------|------|------|------|------|------|
| 18 | 1.25 | 5 | 5 | 5 | 2 | 5 | 2 |
| 27 | 1.25 | 5 | 5 | 5 | 5 | 5 | 5 |
| 29 | 1.25 | 5 | 5 | 5 | 3 | 5 | 2 |
| 33 | 1.25 | 5 | 5 | 5 | 4 | 5 | 2 |
| 35 | 1.25 | 5 | 5 | 5 | 5 | 5 | 3 |
| 42 | 1.25 | 4 | 4 | 1 | 2 | 2 | 0 |
| 54 | 1.25 | 5 | 5 | 5 | 5 | 5 | 5 |
| 63 | 1.25 | 5 | 5 | 5 | 5 | 5 | 5 |
| 65 | 1.25 | 5 | 5 | 5 | 5 | 5 | 3 |
| 69 | 1.25 | 5 | 5 | 5 | 5 | 5 | 3 |
| 71 | 1.25 | 5 | 5 | 5 | 5 | 5 | 4 |
| 76 | 1.25 | 5 | 5 | 5 | 5 | 5 | 3 |
| 78 | 1.25 | 5 | 5 | 5 | 4 | 5 | 3 |

Abbreviations:
STME = Stellaria media
CRSE = Chrysanthemum segetum
SIAL = Sinapis alba
LOMU = Lolium multiflorum
ECCR = Echinochloa crus-galli
VSA = Avena sativa
a.i. = active ingredient (= based on pure active substance)

A similarly good pre-emergence effect as in the examples mentioned in Table 2 is also shown, for example, by the compounds of Examples 23, 40, 31, 57, 59, 61 and 67 from Table 1 against harmful plants such as Avena fatua, Alopecurus myosuroides, Setaria pumila, Poa annua, Stellaria media, Pharbitis purpura, Lolium multiflorum, Echinochloa crus-galli, Cyperus esculentus, Sinapis alba, Galium aparine, Chrysanthemum segetum, Matricaria inodora and Amaranthus retroflexus 2. Post-emergence effect on weeds Seeds or rhizome pieces of monocotyledon and dicotyledon weeds were placed in sandy loam soil in plastic pots, covered with soil and grown in a greenhouse under good growth conditions. Three weeks after sowing, the test plants were treated in the three-leaf stage.

The compounds according to the invention which were formulated as wettable powders or as emulsion concentrates were sprayed in various dosages on the green parts of the plants at an application rate of 600 to 800 l of water/ha (converted) and, after the test plants had remained in the greenhouse for about 3 to 4 weeks under ideal growth conditions, the effect of the preparations was scored visually by comparison with untreated controls.

The agents according to the invention also have a good herbicidal post-emergence action against a broad range of economically important grass weeds and dicotyledon weeds (cf. Table 3).

TABLE 3

Post-emergence effect of the compounds according to the invention

| Ex. No. | Dosage rate (kg of a.i./ha) | STME | CRSE | SIAL | LOMU | ECCR | AVSA |
|---|---|---|---|---|---|---|---|
| 18 | 1.25 | 5 | 2 | 5 | 1 | 4 | 1 |
| 27 | 1.25 | 4 | 4 | 5 | 4 | 4 | 3 |
| 29 | 1.25 | 4 | 3 | 5 | 1 | 4 | 0 |
| 33 | 1.25 | 5 | 4 | 5 | 2 | 3 | 3 |
| 35 | 1.25 | 5 | 3 | 4 | 4 | 5 | 3 |
| 42 | 1.25 | 3 | 3 | 3 | 0 | 1 | 0 |
| 54 | 1.25 | 5 | 5 | 5 | 3 | 5 | 1 |
| 63 | 1.25 | 5 | 4 | 5 | 5 | 5 | 2 |
| 65 | 1.25 | 5 | 5 | 5 | 3 | 5 | 2 |
| 69 | 1.25 | 5 | 4 | 5 | 4 | 5 | 3 |
| 71 | 1.25 | 5 | 3 | 5 | 5 | 4 | 4 |
| 76 | 1.25 | 5 | 5 | 5 | 5 | 5 | 2 |
| 78 | 1.25 | 4 | 4 | 5 | 1 | 4 | 0 |

Abbreviations: see Table 2

A similarly good pre-emergence effect as in the examples mentioned in Table 3 is also shown, for example, by the compounds of Examples 23, 40, 31, 57, 59, 61 and 67 from Table 1 against harmful plants such as Avena fatua, Alopecurus myosuroides, Setaria pumila, Poa annua, Stellaria media, Pharbitis purpura, Lolium multiflorum, Echinochloa crus-galli, Cyperus esculentus, Sinapis alba, Galium aparine, Chrysanthemum segetum, Matricaria inodora and Amaranthus retroflexus.

3. Tolerance by crop plants

In further greenhouse experiments, seeds of a substantial number of crop plants and weeds were placed in sandy loam soil and covered with soil.

Some of the pots were treated immediately as described under 1., and the remaining pots were placed in a greenhouse until the plants had developed two to three true leaves and then sprayed with various dosage rates of the substances according to the invention, as described under 2. Visual scoring four to five weeks after the application and after the plants had been in the greenhouse revealed that the compounds according to the invention did not inflict any damage to dicotyledon crops such as, for example, soya, cotton, oilseed rape, sugar beet and potatoes when used pre- and post-emergence, even when high dosages of active substance were used. Moreover, some substances also left Gramineae crops such as, for example, barley, wheat, rye, Sorghum species, maize or rice unharmed. The compounds of the formula (I) therefore have a high selectivity when used for controlling undesired plant growth in agricultural crops.

We claim:

1. A compound of the formula (I) or a salt thereof,

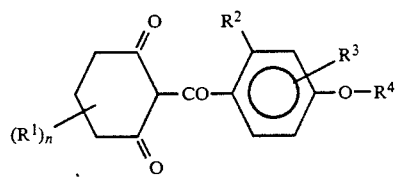

(I)

in which n is an integer from 0 to 6, $R^1$ represents identical or different substituents selected from the group consisting of straight-chain $C_1$-$C_4$-alkyl, branched $C_3$-$C_4$-alkyl, $C_3$-$C_6$-cycloalkyl and phenyl, the abovementioned radicals being unsubstituted or substituted by one or more halogen atoms, $R^2$ is halogen, $NO_2$, CN, $C_1$-$C_3$-alkyl, $C_1$-$C_3$-haloalkyl, $C_1$-$C_3$-alkoxy, $C_1$-$C_3$-haloalkoxy, $C_1$-$C_3$-thioalkyl, $R^aSO_2$—, $R^aSO_2$—O—, $R^aSO_2NR^b$—, where $R^a$ and $R^b$ independently of one another are $C_1$-$C_2$-alkyl or $C_1$-$C_2$-haloalkyl, $R^3$ is hydrogen, halogen, $C_1$-$C_3$-alkyl, $C_1$-$C_3$-haloalkyl, $C_1$-$C_3$-alkoxy, $C_1$-$C_3$-haloalkoxy or $C_1$-$C_3$-alkylthio and $R^4$ is $C_1$-$C_3$-haloalkyl.

2. A compound of the formula (I) or a salt thereof as claimed in claim 1, wherein n is an integer from 0 to 4, $R^1$ represents identical or or different substituents selected from the group consisting of straight-chain $C_1$-$C_3$-alkyl, i-propyl, $C_4$-$C_6$-cycloalkyl and phenyl, the above 4 radicals being unsubstituted or substituted by one or more radicals selected from the group consisting of chlorine and fluorine, $R^2$ is halogen, $NO_2$, CN, $C_1$-$C_3$-alkyl, $C_1$-$C_3$-haloalkyl, $C_1$-$C_2$-alkoxy, $C_1$-$C_2$-haloalkoxy, $R^aSO_2$—, where $R^a$ is $C_1$-$C_2$-alkyl or $C_1$-$C_2$-haloalkyl, is H, halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio and $R^4$ is $C_1$-$C_3$-haloalkyl.

3. A compound of the formula (I) or a salt thereof as claimed in claim 1, wherein n is 0 to 3;

$R^1$ is $C_1$-$C_3$-alkyl, cyclopentyl or phenyl;

$R^2$ is fluorine, chlorine, $NO_2$, CN, methyl, trifluoromethyl, methoxy, difluoromethoxy, trifluoromethoxy or methylsulfonyl;

$R^3$ is hydrogen, halogen, methyl, $CF_3$, methoxy, difluoromethoxy, trifluoromethoxy or methylthio, and $R^4$ is $CH_2F$, $CHF_2$, $CH_2Cl$, $CHCl_2$, $CCl_3$, $CH_2CH_2Cl$, $CH_2CH_2F$, $CH_2CHF_2$, $CH_2CF_3$, $CHFCH_3$, $CHFCH_2F$, $CHFCHF_2$, $CF_2CH_3$, $CF_2CH_2F$, $CF_2CHF_2$, $CF_2CF_3$, $CF_2CHFCl$, $CHFCHFCl$, $CH_2CCl_3$, $CH_2CHCl_2$, $CHFCHCl_2$, $CF_2CHCl_2$, $CHFCH_2Cl$ or $Cf_2CH_2Cl$.

4. The compound of the formula (I) or a salt thereof as claimed in claim 3, wherein $R^4$ is $CHF_2$ or $CF_2CHFCl$.

5. The compound of the formula (I) or a salt thereof as claimed in claim 4, wherein n is an integer from 0 to 3, $R^1$ is methyl, $R^2$ is fluorine, chlorine or $NO_2$, and $R^3$ is hydrogen.

6. The compound of the formula (I) or a salt thereof as claimed in claim 5, wherein $R^4$ is $CF_2H$.

7. The compound of the formula (I) or a salt thereof as claimed in claim 6, wherein $(R^1)_n$ is 4,4,6-$(CH_3)_3$, $R^2$ is $NO_2$ and $R^3$ is H.

8. A herbicidal or plant-growth-regulating agent, which comprises a compound of the formula (I) or a salt thereof as claimed in claim 1, and customary formulation auxiliaries.

9. A herbicidal or plant-growth-regulating agent, which comprises a compound of the formula (I) or a salt thereof as claimed in claim 2, and customary formulation auxiliaries.

10. A method for selectively controlling harmful plants, which comprises applying an effective amount of one of the compounds of the formula I or a salt thereof as defined in claim 1 to the plants, seeds of the plants or the area under cultivation.

11. A method for regulating the growth of plants, which comprises applying an effective amount of one of the compounds of the formula I or a salt thereof as defined in claim 1 to the plants, seeds of the plants or the area under cultivation.

* * * * *